United States Patent
Na et al.

(10) Patent No.: US 12,232,903 B2
(45) Date of Patent: Feb. 25, 2025

(54) X-RAY IMAGING APPARATUS

(71) Applicants: VATECH Co., Ltd., Gyeonggi-do (KR); VATECH EWOO Holdings Co., Ltd., Gyeonggi-do (KR)

(72) Inventors: Han Sik Na, Gyeonggi-do (KR); Da Hea Han, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 265 days.

(21) Appl. No.: 17/830,605

(22) Filed: Jun. 2, 2022

(65) Prior Publication Data

US 2022/0386971 A1 Dec. 8, 2022

(30) Foreign Application Priority Data

Jun. 3, 2021 (KR) .......... 10-2021-0072424
Jun. 14, 2021 (KR) .......... 10-2021-0076905

(51) Int. Cl.
*A61B 6/51* (2024.01)
*A61B 6/00* (2024.01)

(52) U.S. Cl.
CPC .......... *A61B 6/51* (2024.01); *A61B 6/4452* (2013.01)

(58) Field of Classification Search
CPC ........ A61B 6/51; A61B 6/4452; A61B 6/0407
See application file for complete search history.

(56) References Cited

U.S. PATENT DOCUMENTS

| 2007/0041491 A1* | 2/2007 | Sadakane | A61B 6/032 378/15 |
|---|---|---|---|
| 2010/0054403 A1 | 3/2010 | Ro et al. | |
| 2013/0307923 A1 | 11/2013 | Inglese et al. | |
| 2014/0254750 A1 | 9/2014 | Yoshimura et al. | |

(Continued)

FOREIGN PATENT DOCUMENTS

| CN | 102413770 | * 6/2014 | ............ A61B 6/035 |
|---|---|---|---|
| EP | 3469991 A1 | 4/2019 | |

(Continued)

OTHER PUBLICATIONS

European Patent Office, European Search Report of corresponding EP Patent Application No. 22176018.4, Oct. 21, 2022.

*Primary Examiner* — David P Porta
*Assistant Examiner* — Meenakshi S Sahu
(74) *Attorney, Agent, or Firm* — IP Legal Services, LLC

(57) ABSTRACT

An X-ray imaging apparatus is proposed. The X-ray imaging apparatus is configured to capture first and second X-ray images having examination object's alignment positions different from each other, the X-ray imaging apparatus including an imaging part configured to include a generator and a detector facing each other with an examination object interposed therebetween, and rotate the generator and the detector about a rotation axis therebetween to capture each of the first and second X-ray images, and an examination object alignment part configured to arrange the examination object between the generator and the detector, wherein a position of at least a part of the examination object alignment part is variable, so as to move and align the examination object to a first alignment position for capturing the first X-ray image and a second alignment position for capturing the second X-ray image, respectively.

6 Claims, 11 Drawing Sheets

(56) References Cited

U.S. PATENT DOCUMENTS

2015/0004558 A1 1/2015 Inglese et al.
2017/0311910 A1 11/2017 Inglese et al.
2018/0368673 A1 12/2018 Inglese et al.
2019/0053775 A1 2/2019 Arai et al.

FOREIGN PATENT DOCUMENTS

| JP | 2007-029168 A | 2/2007 |
| JP | 2013-244145 A | 12/2013 |
| JP | 2014-195644 A | 10/2014 |
| KR | 10-1990-0007542 B1 | 10/1990 |
| WO | 2008/072821 A1 | 6/2008 |

* cited by examiner

X-RAY IMAGING APPARATUS

CROSS REFERENCE TO RELATED APPLICATION

The present application claims priority to Korean Patent Application Nos. 10-2021-0072424, filed Jun. 3, 2021 and 10-2021-0076905, filed Jun. 14, 2021, the entire contents of which is incorporated herein for all purposes by this reference.

BACKGROUND OF THE INVENTION

Field of the Invention

The present disclosure relates to an X-ray imaging apparatus and, more particularly, to an X-ray imaging apparatus for capturing first and second X-ray images respectively having different alignment positions of an examination object relative to the apparatus.

Description of the Related Art

X-ray imaging is a method of radiography using the transmittance and straightness of X-rays, and differences in X-ray transmissivity according to an internal structure of an object to be imaged are displayed as an X-ray image in gray levels on the basis of X-ray attenuation accumulated during a process of transmitting through the object to be imaged.

An X-ray imaging apparatus is composed of necessary components including: an X-ray generator (hereinafter, referred to as a generator) configured to emit X-rays toward an object to be imaged; an X-ray detector (hereinafter referred to as a detector) configured to detect X-rays transmitting through the object to be imaged and generate X-ray projection data in which a relative difference between X-ray doses for each position is reflected; and an image processor configured to realize an X-ray image of the object to be imaged by using the X-ray projection data.

X-ray images may be classified in various ways. For example, X-ray panoramic images and Computed Tomography (CT) images of the dental arch are mainly used in the field of dentistry, where teeth and tissues surrounding the teeth are areas of interest.

An X-ray panoramic image shows a three-dimensional structure of the dental arch including upper and lower jaws spread out on a plane. The X-ray panoramic image is useful for fundamental diagnosis because of illustrating a comprehensive plan view of the three-dimensional structure of the dental arch. A CT image represents the three-dimensional structure of the dental arch as a three-dimensional voxel. The CT image may accurately express not only the three-dimensional structure of the dental arch, but also cross sections of desired positions and directions, so the CT image is useful in planning a high precision-required treatment such as an implant.

As the types of X-ray images are diversified, a so-called multimodality X-ray imaging apparatus capable of capturing different X-ray images with a single apparatus has been introduced and is widely used. For example, in dentistry, a combined X-ray panoramic and computed tomography (CT) X-ray imaging apparatus capable of capturing an X-ray panoramic image and a CT image with the single apparatus is used.

In a general combined panoramic and CT X-ray imaging apparatus, a patient's head, which is an examination object, is supported by an examination object support and aligned in an imaging position, a generator and a detector are arranged at opposite ends of a rotary arm, which is a predetermined mechanism, face each other with the examination object interposed therebetween, and the rotary arm rotates and/or moves about a rotation axis present therebetween to capture the X-ray panoramic image or CT image.

Meanwhile, imaging positions, that is, alignment positions of an examination object relative to the generator and detector are different from each other in the X-ray panoramic image and CT image. For this reason, the rotary arm is configured to be movable in the general combined panoramic and CT X-ray imaging apparatus, and the generator and detector move to respective imaging positions by the movement of the rotary arm during X-ray panoramic imaging and CT imaging.

However, separate mechanical components are required to move the rotary arm, thereby causing an increase in design and manufacturing costs. In addition, considering that the weight of the generator, detector, and rotary arm weighs quite a bit, the movement of the rotary arm substantially moves the center of gravity of the X-ray imaging apparatus, so another components are required to solve this issue, whereby there is a problem in that the apparatus is enlarged and complicated.

SUMMARY OF THE INVENTION

An objective of the present disclosure is to solve the above problems. That is, the present disclosure relates to an X-ray imaging apparatus for capturing first and second X-ray images in which alignment positions of an examination object relative to the apparatus are different from each other, and the objective of the present disclosure is to provide the X-ray imaging apparatus capable of moving and aligning the examination object to each alignment position without moving a rotary arm.

In order to achieve the above objective, there is provided an X-ray imaging apparatus configured to capture first and second X-ray images having examination object's alignment positions different from each other, the X-ray imaging apparatus including: an imaging part configured to comprise a generator and a detector facing each other with an examination object interposed therebetween, and rotate the generator and the detector about a rotation axis therebetween to capture each of the first and second X-ray images; and an examination object alignment part configured to arrange the examination object between the generator and the detector, wherein a position of at least a part of the examination object alignment part is variable, so as to move and align the examination object to a first alignment position for capturing the first X-ray image and a second alignment position for capturing the second X-ray image, respectively.

In addition, the X-ray imaging apparatus may further include a main body configured to support the rotation axis, wherein the examination object alignment part may further include: a frame connected to the main body; and an examination object support configured to support the examination object and move in reciprocation between a first reference position for aligning the examination object to the first alignment position and a second reference position for aligning the examination object to the second alignment position along the frame.

In addition, the examination object alignment part may further include a sensing means configured to detect positions of the examination object support relative to the frame.

In addition, the examination object alignment part may further include a driving controller configured to control, according to detection results of the sensing means, the imaging part to capture the first X-ray image when the examination object support is positioned at a first reference position and to capture the second X-ray image when the examination object support is positioned at a second reference position.

In addition, the X-ray imaging apparatus may further include a guide rail installed on the frame, wherein the examination object support may move in reciprocation between the first and second reference positions along the guide rail.

In addition, the X-ray imaging apparatus may further include first and second stopper holders installed to be spaced apart from each other along the guide rail to restrict respective movements of the examination object support, wherein the examination object support may move in reciprocation between the first reference position provided by the first stopper holder and the second reference position provided by the second stopper holder.

In addition, the examination object support may further include a moving block configured to move along the guide rail; and first and second stopper protrusions respectively provided at front and rear ends of the moving block in a movement direction to be press-fitted respectively to the first and second stopper holders.

In addition, the examination object support may be connected to an end of the frame and move along a longitudinal direction of the frame.

In addition, the examination object support may accommodate the end of the frame therein and move along the longitudinal direction of the frame according to a degree of accommodation of the end.

In addition, the examination object may be a patient's head including the dental arch, the first X-ray image may be an image of CT imaging, the first alignment position may be a position at which the rotation axis coincides with a center of an imaging area (FOV), the second X-ray image may be an X-ray panoramic image, and the first alignment position may be a position at which the rotation axis is arranged, inside the dental arch, on a midline of the dental arch.

The present disclosure relates to the X-ray imaging apparatus capable of capturing the first and second X-ray images having imaging positions different from each other, and capable of moving and aligning the examination object to each imaging position without moving the rotary arm. Accordingly, there is an advantage in that the mechanical components for moving the rotary arm may be omitted or reduced, so that the apparatus may be miniaturized and simplified.

25

DETAILED DESCRIPTION OF THE INVENTION

Hereinafter, a preferred exemplary embodiment of the present disclosure will be described with reference to the drawings.

Figure 1:
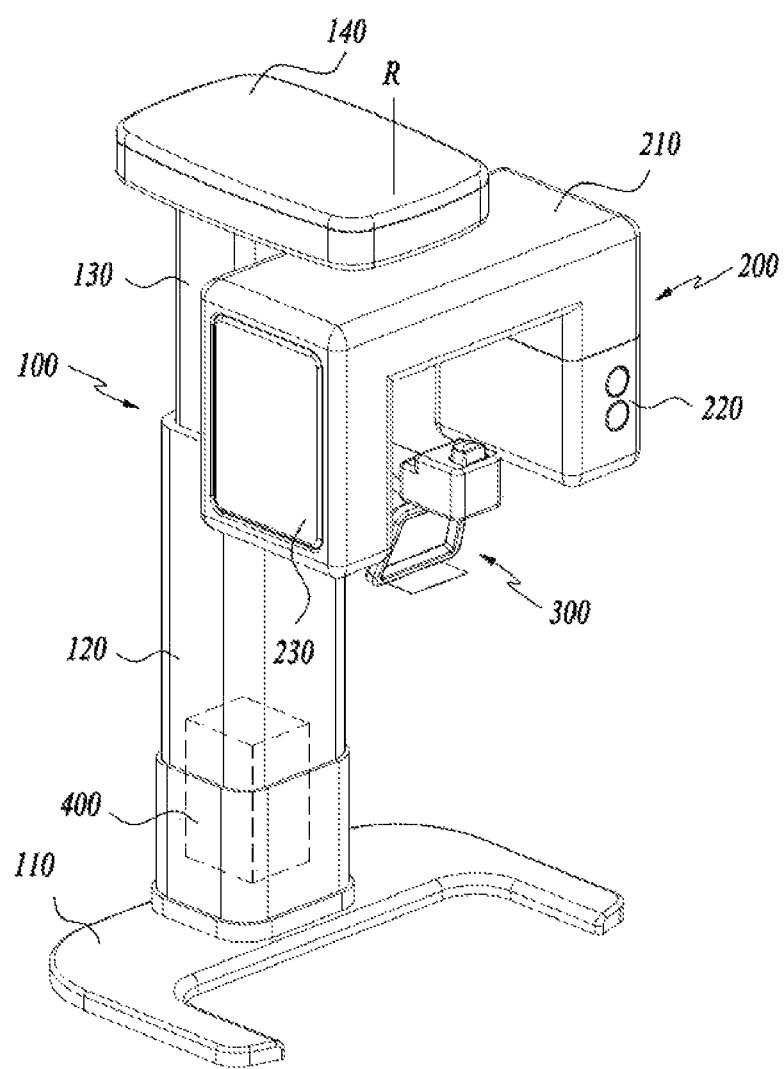
FIG. 1 is a view illustrating an X-ray imaging apparatus according to the present disclosure.

FIG. 1 is a view illustrating an X-ray imaging apparatus according to the present disclosure. Hereinafter, a dental X-ray imaging apparatus will be described as an example for convenience, but the present disclosure is not limited thereto.

The X-ray imaging apparatus according to the present disclosure includes a main body 100, an imaging part 200, an examination object alignment part 300, a driving controller 400, and an image processor (not shown).

The main body 100 is configured to support the X-ray imaging apparatus according to the present disclosure, and includes a base 110 seated on a floor, a column 120 vertically connected to the base 110, a lifting arm 130 connected to the column 120 to be movable up and down, and a support arm 140 vertically connected to the lifting arm 130. However, the present disclosure is not limited thereto, and instead of omitting the base 110, various modifications are possible such that the column 120 is directly fixed to the floor or mounted on a wall.

The imaging part 200 is configured to capture first and second X-ray images of an examination object, and includes: a rotary arm 210 connected to the support arm 140 by a rotation axis R; and a generator part 220 and a detector part 230 respectively arranged, to face with each other, at opposite ends of the rotary arm 210 provided with the rotation axis R interposed in between. The generator part 220 and the detector part 230 are respectively provided with a generator and a detector.

The examination object alignment part 300 is configured to align the examination object between the generator part 220 and the detector part 230. In the X-ray imaging apparatus according to the present disclosure, instead of fixing a position of the rotation axis R of the rotary arm 210, a position of at least a part of the examination object alignment part 300 is variable, so that the examination object is moved and aligned to each of a first alignment position for first X-ray imaging and a second alignment position for second X-ray imaging. The examination object alignment part 300 will be described in detail in corresponding sections.

The driving controller 400 is configured to control the first and second X-ray imaging by the imaging part 200, and controls rotation of the rotary arm 210, X-ray emission of the generator, and X-ray detection of the detector according to user's imaging signals. In particular, the driving controller 400 controls the imaging part 200 to capture the first X-ray image when the examination object alignment part 300 aligns the examination object at the first alignment position, and to capture the second X-ray image when the examination object alignment part 300 aligns the examination object at the second alignment position. In addition, the driving controller 400 may control various support operations for capturing the first and second X-ray images, such as adjusting the height of the lifting arm 130 relative to the column 120 according to user's operation signals.

The image processor reconstructs the first X-ray image by using first projection data obtained by the first X-ray imaging, and reconstructs the second X-ray image by using second projection data obtained by the second X-ray imaging. To this end, the image processor may include a computer and the like, on which a predetermined reconstruction algorithm is loaded, and for example, the first and second X-ray images may be respectively a CT image and an X-ray panoramic image.

Figure 2:
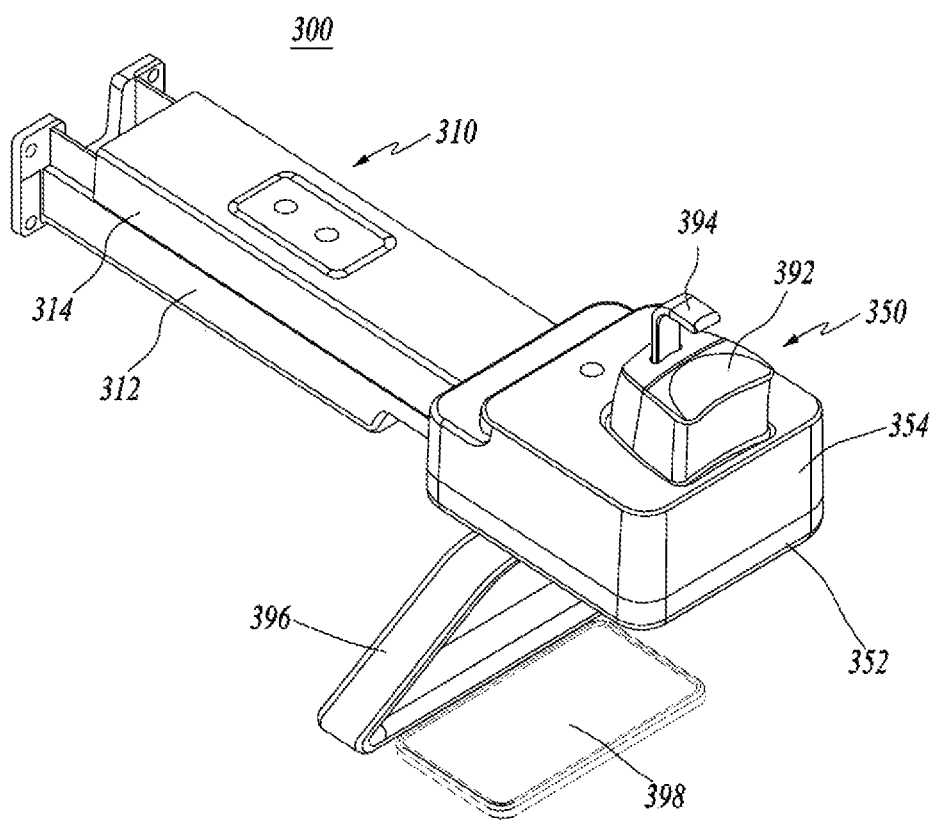
FIG. 2 is a view illustrating an examination object alignment part of the X-ray imaging apparatus according to the present disclosure.

FIG. 2 is a view illustrating the examination object alignment part of the X-ray imaging apparatus according to the present disclosure. Reference is made in conjunction with FIG. 1 described above.

The examination object alignment part 300 of the X-ray imaging apparatus according to the present disclosure includes: a frame 310 connected to the main body 100; and an examination object support 350 configured to support an examination object and move along the frame 310.

While providing a movement path for movement of the examination object support 350, the frame 310 connects the main body 100 and the examination object support 350 to each other so as to support the examination object support 350. The frame 310 may include: a base frame 312 configured to have one end thereof connected to the main body 100, for example, to a lifting arm 130; and a frame cover 314 configured to cover the base frame 312.

The examination object support 350 is connected to the frame 310 to directly support the examination object, and moves in reciprocation between a first reference position for aligning the examination object to the first alignment position and a second reference position for aligning the examination object to the second alignment position. The examination object support 350 may include a base plate 352 and a plate cover 354 for covering the base plate 352, and the plate cover 354 may be provided with a predetermined mechanism for supporting the examination object. For example, the mechanism may include: a chinrest 392 on which the examinee's chin is seated; and a bite 394 connected to the chinrest 392 and which the examinee, with his or her chin placed on the chinrest 392, bites with his or her mouth.

Accordingly, when the examination object support 350 moves to the first reference position, the examination object is aligned to the first alignment position, and when the examination object support 350 moves to the second reference position, the examination object is aligned to the second alignment position.

In addition, the examination object alignment part 300 may include a handle 396 connected to a lower end of the frame 310 or examination object support 350 and gripped by the examinee's hand; a shelf 398 connected to the handle 396 and on which the examinee's accessories and the like may be placed; and the like.

Figure 3:
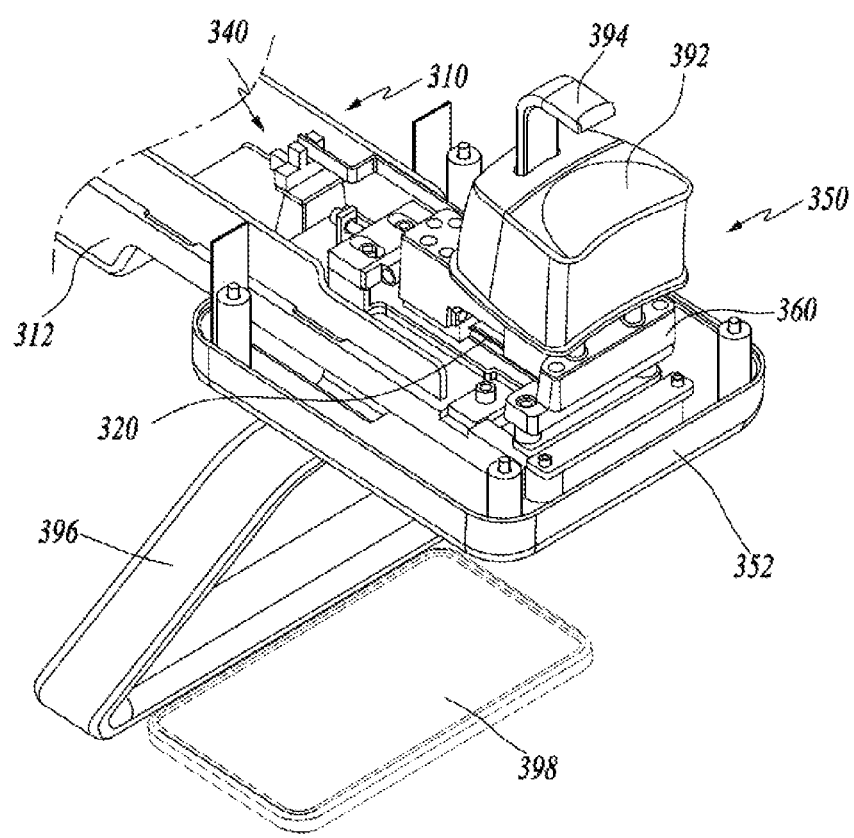
FIGS. 3 and 4 are views respectively illustrating internal structures of the examination object alignment part of the X-ray imaging apparatus according to the present disclosure.
Figure 4:
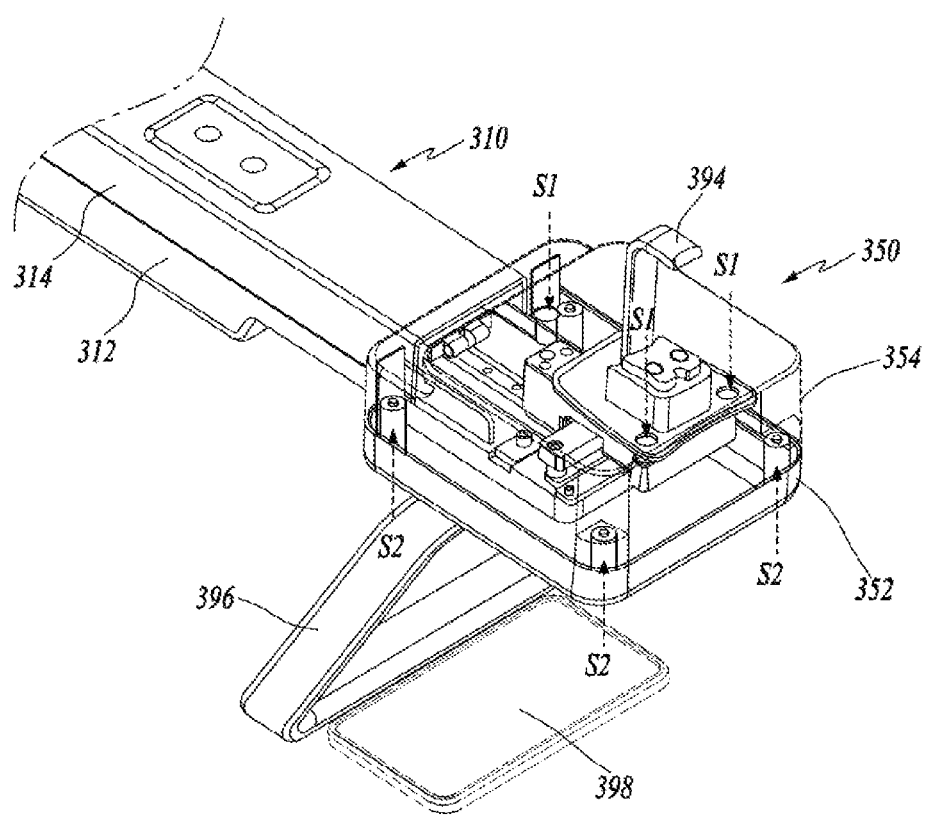

FIGS. 3 and 4 are views respectively illustrating internal structures of the examination object alignment part of the X-ray imaging apparatus according to the present disclosure. FIG. 3 is a view in which the frame cover 314 of the frame 310 and the plate cover 354 of the examination object support 350 are removed, and FIG. 4 is a view illustrating the plate cover 354 of the examination object support 350 with a hidden line.

The frame 310 includes a guide rail 320 installed on the base frame 312, and the examination object support 350 includes a moving block 360 installed movably along the guide rail 320. In addition, the plate cover 354 of the examination object support 350 may be fixed to the moving block 360 with a first screw S1 or the like. The base plate 352 may maintain a predetermined distance from the base frame 312 at the lower end of the base frame 312, and may be fixed to the plate cover 354 with a second screw S2 or the like. The chinrest 392 may be fixed to the moving block 360, and may be exposed to outside through the plate cover 354.

Accordingly, when a user moves the examination object support 350 along a longitudinal direction of the guide rail 320, the examination object support 350 including the moving block 360 may move along the frame 310.

For example, the guide rail 320 may be installed along the longitudinal direction of the frame 310 at an end of the base frame 312, and the examination object support 350 may move along the longitudinal direction of the frame 310 so that the degree of accommodation is adjusted while accommodating an end of the frame 310 therein. However, the present disclosure is not limited thereto, and it is also possible that the guide rail 320 is arranged at the end of the base frame 312 in a direction crossing the longitudinal direction of the frame 310 so that the examination object support 350 moves in the direction crossing the longitudinal direction of the frame 310 while accommodating the end of the frame 310 therein.

Figure 5:
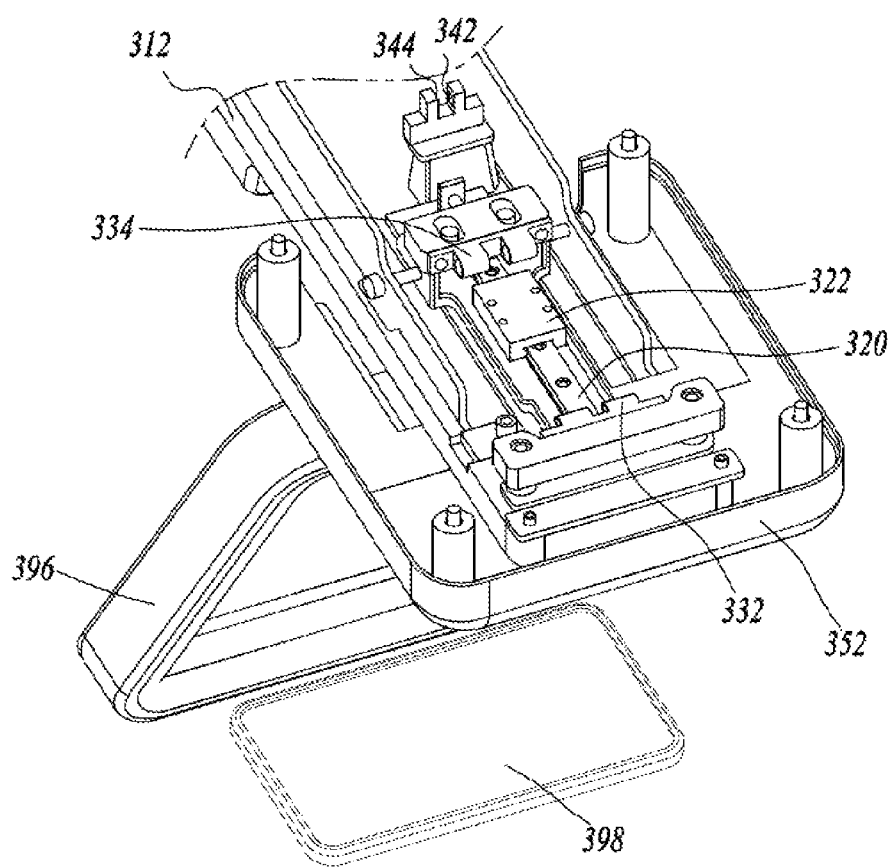
FIG. 5 is a view illustrating a part of the examination object alignment part of the X-ray imaging apparatus according to the present disclosure.
Figure 6:
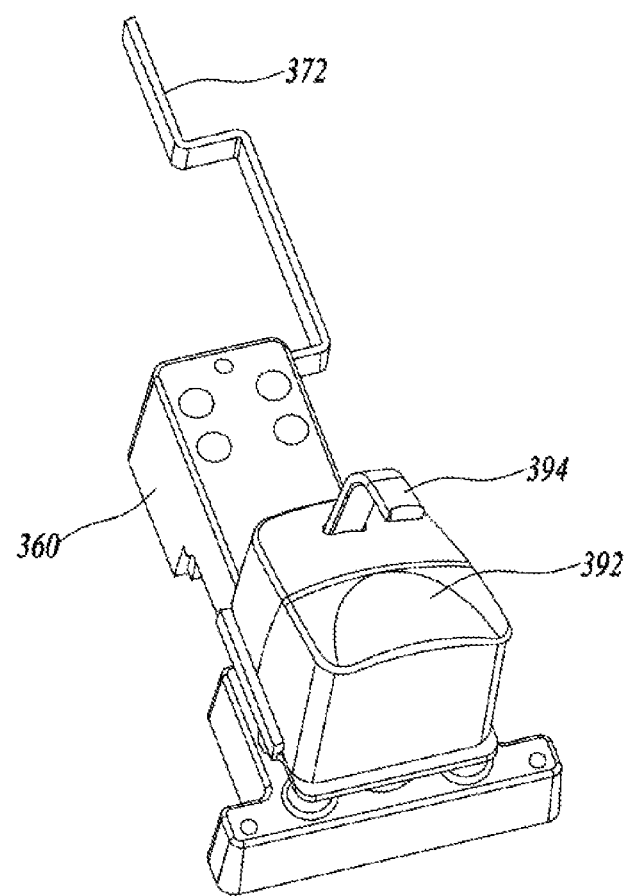
FIGS. 6 and 7 are respective views illustrating a moving block of the examination object alignment part of the X-ray imaging apparatus according to the present disclosure.
Figure 7:
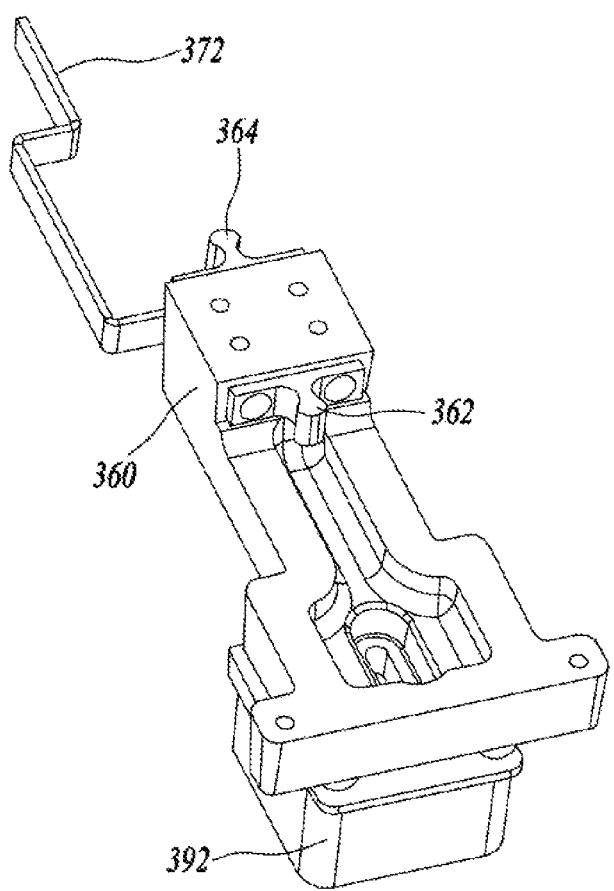

FIG. 5 is a view in which the moving block 360 and components coupled thereto in FIG. 3 are removed, and FIGS. 6 and 7 are respectively a plan view and a bottom perspective view of the moving block 360.

The moving block 360 may be coupled to a slider 322 movable along the guide rail 320, so as to be movable along the guide rail 320. In addition, the first and second stopper holders 332 and 334 configured to face with each other along the guide rail 320 installed on the base frame 312 and to be respectively provided with first and second grooves may be installed to be spaced apart from each other at a predetermined interval, and the first and second stopper protrusions 362 and 364 respectively press-fitted to the first and second stopper holders 332 and 334 may be respectively provided at front and rear ends in the movement direction of the moving block 360. In addition, coupling positions of the first and second stopper holders 332 and 334 and coupling positions of the first and second stopper protrusions 362 and 364 may respectively correspond to the first reference position and the second reference position of the examination object support 350.

Accordingly, when the examination object support 350 moves along the guide rail 320 in any one direction together with the moving block 360 so that the first stopper protrusion 362 is fitted to the first stopper holder 332, the examination object support 350 is fixed to the first reference position, and when the examination object support 350 moves along the guide rail 320 in opposite direction of the one direction together with the moving block 360 so that the second stopper protrusion 364 is fitted to the second stopper holder 334, the examination object support 350 is fixed to the second reference position. The first and second stopper holders 332 and 334 and the first and second stopper protrusions 362 and 364 are configured to fix the examination object support 350 to the respective first and second reference positions and at the same time are press-fitted to each other in order to prevent unnecessary movement of the examination object support 350 during X-ray imaging, and are easily separated from each other when the user applies force.

Figure 8:
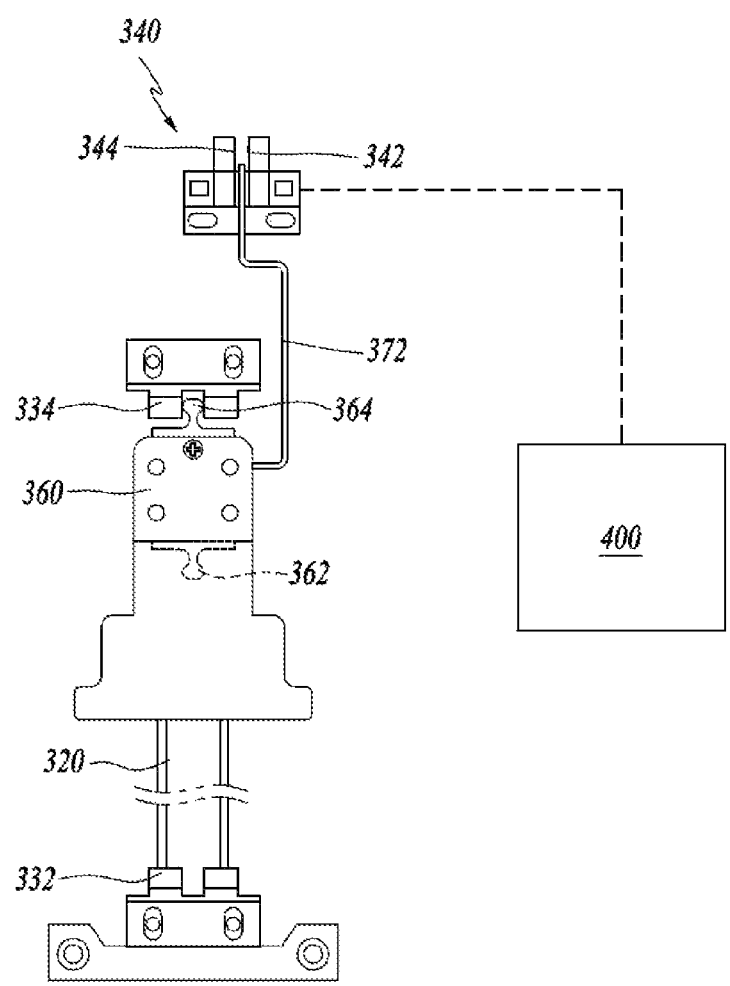
FIGS. 8 and 9 are views respectively illustrating movement states of the moving block of the examination object alignment part of the X-ray imaging apparatus according to the present disclosure.
Figure 9:
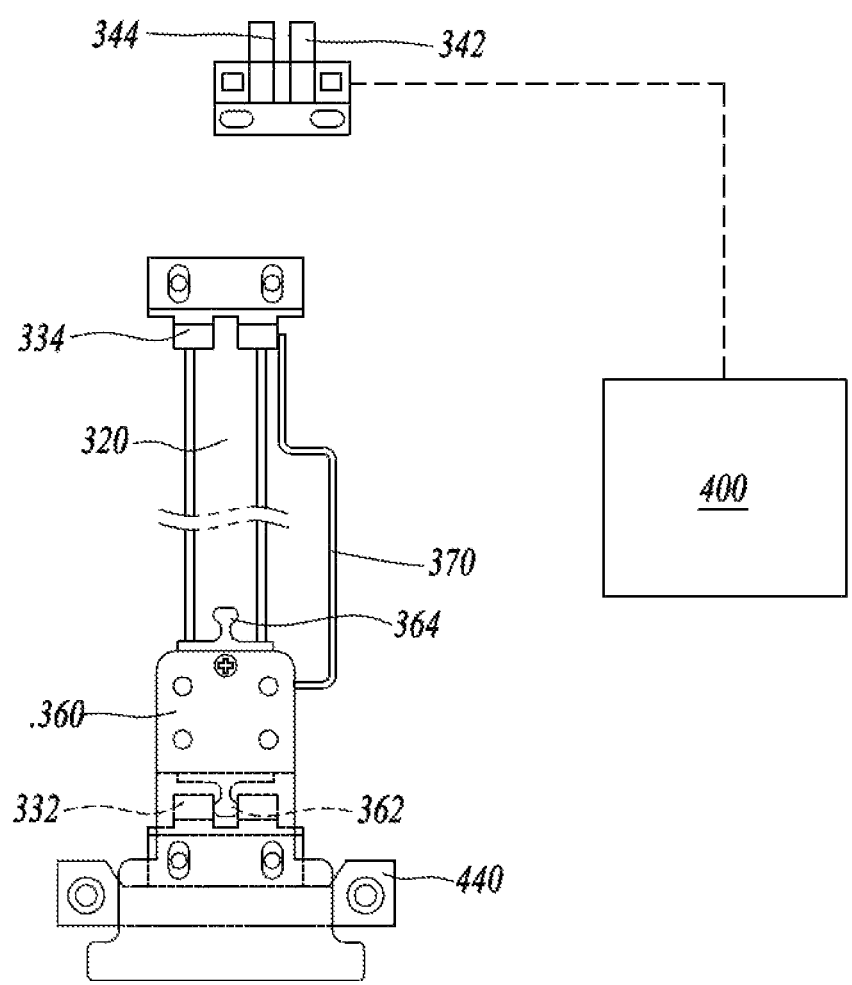

FIGS. 8 and 9 are views respectively illustrating the moving states of the moving block 360 together with the driving controller 400. FIGS. 2 and 3 are referred together.

A sensing means 340 for detecting positions of the examination object support 350 may be provided in the examination object alignment part 300 of the X-ray imaging apparatus according to the present disclosure. In addition, according to detection results of the sensing means 340, the driving controller 400 controls the imaging part 200 to capture the first X-ray image when the examination object support 350 is aligned at the first reference position and to capture the second X-ray image when the examination object support 350 is aligned at the second reference position.

The sensing means 340 may include: a guide pin 372 extending along the movement direction of the moving block 360 from one side of the moving block 360; and a light source 342 and a light sensor 344 that are mounted on one side of the frame 310 and configured to face each other while having a point therebetween at which an end of the guide pin 372 selectively passes by the movement of the moving block 360.

Accordingly, when the examination object support 350 moves to the first reference position in any one direction together with the moving block 360, the end of the guide pin 372 deviates from the point between the light source 342 and the photosensor 344, so that the photosensor 344 detects the light from the light source 342, thereby outputting a first signal. In addition, when the examination object support 350 moves to the second reference position that is a reverse direction of the one direction together with the moving block 360, the end of the guide pin 372 is inserted between the light source 342 and the light sensor 344 so as to block the light emitting from the light source 342 to the light sensor 344, thereby outputting a second signal.

In addition, the first and second signals, which are the detection results of the sensing means 340, are transmitted to the driving controller 400, and according to the first and second signals, the driving controller 400 controls the imaging part 200 to capture the first X-ray image or the second X-ray image by detecting a state in which the examination object support 350 is aligned to any one of the first and second reference positions.

Figure 10A:
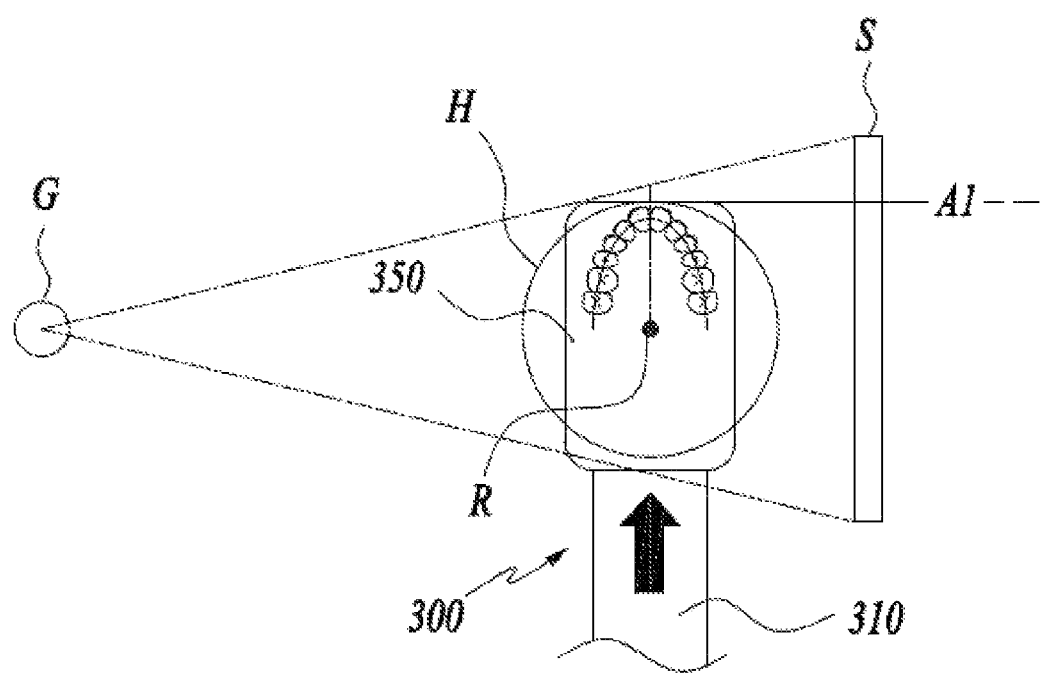
FIGS. 10A and 10B are views respectively illustrating movement states of the examination object alignment part during first and second X-ray imaging of the X-ray imaging apparatus according to the present disclosure.
Figure 10B:
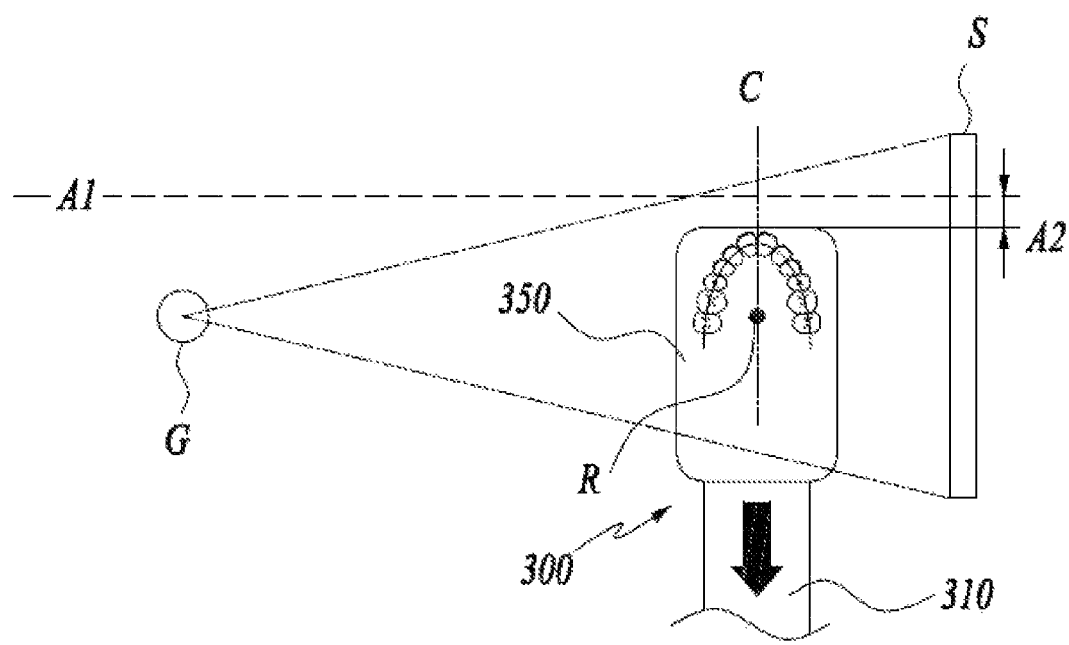

FIGS. 10A and 10B are views respectively illustrating examination object positions provided by the examination object alignment part 300 during first and second X-ray imaging of the X-ray imaging apparatus according to the present disclosure. For convenience, it is assumed that the examination object support 350 moves along the longitudinal direction of the frame 310.

FIG. 10A is a view illustrating the first X-ray imaging. The examination object support 350 moves in any one direction along the frame 310 to be positioned at the first reference position A1, and aligns the examination object to the first alignment position. The first alignment position is for the first X-ray imaging. For example, the first X-ray imaging may be CT imaging of the dental arch, and the first alignment position may be a position at which the rotation axis R coincides with the center of a field of view (FOV), which is a CT imaging area. For reference, the position and size of the FOV may be variously adjusted according to the examination object to be imaged during the CT imaging, and in this case, the center position of the FOV also varies. In addition, the examination object support 350 of the X-ray imaging apparatus according to the present disclosure moves, so as to allow the center R of the FOV to coincide with the rotation axis, whereby the first reference position A1 of the examination object support 350 may also vary depending on the position and size of the FOV. FIG. 10A represents a case where the dental arch is used as the FOV for convenience.

FIG. 10B is a view illustrating the second X-ray imaging. The examination object support 350 arbitrarily moves in the reverse direction of the one direction, that is, toward a front of the first reference position A1 relative to an examinee, to be positioned at the second reference position A2, and aligns the examination object at the second alignment position. The second alignment position is for the second X-ray imaging. For example, the second X-ray imaging may be the X-ray panoramic imaging, and the second alignment position may be a position at which the rotation axis R is arranged on a centerline in a forward and backward direction of the dental arch in the inside of the dental arch, that is, on a midline C.

What is claimed is:

1. An X-ray imaging apparatus configured to capture first and second X-ray images of an object, respectively, the X-ray imaging apparatus comprising:
   an imaging part configured to comprise a generator and a detector facing each other with an object interposed therebetween, and rotate the generator and the detector about a rotation axis therebetween to capture each of the first and second X-ray images; and
   an object alignment part configured to arrange the object between the generator and the detector,
   wherein a position of at least a part of the object alignment part is variable, so as to move and align the object to a first alignment position for capturing the first X-ray image and a second alignment position for capturing the second X-ray image, respectively, and
   wherein the X-ray imaging apparatus further comprises:
   a sensor configured to detect whether a position of at least a part of the object alignment part is a first reference position or a second reference position; and
   a processor configured to control, according to detection results of the sensor, the imaging part to acquire the first X-ray image when at least a part of the alignment part is positioned at the first reference position and to acquire the second X-ray image when the at least a part of the alignment part is positioned at the second reference position.

2. The X-ray imaging apparatus of claim 1, further comprising:
   a main body configured to support the rotation axis,
   wherein the object alignment part further comprises:
   a frame connected to the main body; and
   an object support configured to support the object and move in reciprocation between a first reference position for aligning the object to the first alignment position and a second reference position for aligning the object to the second alignment position along the frame.

3. The X-ray imaging apparatus of claim 2, further comprising:
   a guide rail installed on the frame,
   wherein the object support moves in reciprocation between the first and second reference positions along the guide rail.

4. The X-ray imaging apparatus of claim 3, further comprising:
   first and second stopper holders installed to be spaced apart from each other along the guide rail to restrict respective movements of the object support,
   wherein the object support moves in reciprocation between the first reference position provided by the first stopper holder and the second reference position provided by the second stopper holder.

5. The X-ray imaging apparatus of claim 4, wherein the object support further comprises:
   a moving block configured to move along the guide rail; and
   first and second stopper protrusions respectively provided at front and rear ends of the moving block in a movement direction to be press-fitted respectively to the first and second stopper holders.

6. The X-ray imaging apparatus of claim 1, wherein the object is a patient's head including the dental arch, the first X-ray image is an image of CT imaging, the first alignment position is a position at which the rotation axis coincides with a center of an imaging area (FOV), the second X-ray image is an X-ray panoramic image, and the second alignment position is a position at which the rotation axis is arranged, inside the dental arch, on a midline of the dental arch.

\* \* \* \* \*